United States Patent [19]

Whitfill et al.

[11] Patent Number: 5,057,314

[45] Date of Patent: Oct. 15, 1991

[54] LOW MOLECULAR WEIGHT ANTIVIRAL FACTORS

[76] Inventors: Craig E. Whitfill, 1300 Wellstone Cir., Apex, N.C. 27502; Nicholas R. Gyles, 1336 Northview; John A. Thoma, 1206 Crestwood, both of Fayetteville, Ark. 72702

[21] Appl. No.: 368,557

[22] Filed: Jun. 20, 1989
(Under 37 CFR 1.47)

Related U.S. Application Data

[63] Continuation-in-part of Ser. No. 252,554, Sep. 30, 1988, abandoned, and a continuation-in-part of Ser. No. 252,187, Sep. 30, 1988, abandoned.

[51] Int. Cl.[5] .................... A61K 39/215; A61K 35/16
[52] U.S. Cl. ........................................ 424/89; 424/93; 424/531
[58] Field of Search ............................ 424/89, 93, 531

[56] References Cited

PUBLICATIONS

Whitfill et al., "Isolation of High & Low Molecular Weight Components . . .", Poultry Science 61:1573-78 (1982).

Whitfill et al., "Time Course of Production of Low Molecular Weight Viral Neutralizing Substance(s) in Chickens", BA77(8): 60877.

*Primary Examiner*—Douglas W. Robinson
*Assistant Examiner*—Jean Witz
*Attorney, Agent, or Firm*—Hill, Van Santen, Steadman & Simpson

[57] ABSTRACT

The present invention provides a low molecular weight anti-viral factors isolated from the serum of a hyperimmune regressor line chicken and methods of purifying same. The factors are useful in the treatment and prevention of certain disease states.

12 Claims, No Drawings

LOW MOLECULAR WEIGHT ANTIVIRAL FACTORS

This is a continuation-in-part of U.S. patent application Ser. Nos. 07/252,554 and 07/252,187 both of which were filed on Sept. 30, 1988 both now abandoned.

BACKGROUND OF THE INVENTION

The present invention relates generally to vaccines, the treatment of viruses, and the purification of compounds useful for the same. More specifically, the present invention relates to the use and preparation of low molecular weight factors having anti-viral properties.

Gyles et al., 47 *Poultry Sci.* 430 (1968), and Gyles and Brown, 50 *Poultry Sci.* 901 (1971), likewise reported that regression of Rous sarcoma virus (RSV)-induced tumors is under genetic control in chickens. Further, Schierman et al., 5 *Immunogenetics* 325 (1977), and Collins et al., 5 *Immunogenetics* 333 (1977), have identified a single dominantly inherited gene, designated R-Rs-1, located outside the B blood locus, which appears to be the primary genetic factor regulating regression in chickens.

Differences between the regressor and progressor chickens in early recognition and speed and intensity of response by their immunological systems may be an important key to regression. Gyles et al., 46 *Poultry Sci.* 465 (1967), found that the time required for a tumor to be initiated from wing-web inoculation of RSV varied among genetic lines and among individuals within a genetic line. Gyles et al., 56 *Poultry Sci.* 758 (1977), discovered that the immune response to a secondary RSV challenge with either RSV or Rous sarcoma tumor homogenate (RSTH) in the opposite wing-web was met by an earlier immune response in the regressor line (R-line) than in the progressor line (Pr-line), but that both lines could mount a response to the second challenge.

Our search for a low molecular weight factor (LMF) present in chicken sera that may exhibit viral-neutralizing or anti-tumor activity was stimulated by the discoveries of Burzynski et al., 9 *Physiol. Chem. Phys.* 485 (1977). They have isolated and identified a class of peptides present in sera and urine of normal patients that are potent inhibitors of some human neoplasms. See also Beall et al., 3 *Cancer Biochem. Biophys.* 93 (1979).

As reported by Whitfill et al., 61 *Poultry Sci.* 1573 (1982), a low molecular weight fraction (less than 5000 daltons) was isolated by gel permeation chromatography from chicken sera. This fraction possessed virus-neutralizing capacity and appeared to be present at high levels in regressor chicken hyperimmune sera, a sera obtained from regressor chickens that had fully regressed Rous sarcomas and had also received a secondary booster inoculation of Rous sarcoma tumor homogenate before the blood was removed by cardiac puncture. However, high levels of activity was not found in regressor chicken sera obtained before initial RSV challenge or 32 days after challenge when the tumors completely regressed. Both the regressor and progressor chickens respond to the viral challenge by developing tumors, but the Rous virus elicits a more rapid and intense anti-tumor response in regressor chickens. The active low molecular weight fraction is called the low molecular weight viral neutralizing factor (LMF).

Whitfill, "Time Course of Production of Low Molecular Weight Viral-Neutralizing Substance(s) in Chickens," 17 *Springer/Immunogenetics* 387 (1983), discusses how low molecular weight neutralizing factors can be isolated from blood of the regressor line chickens.

Gyles and Whitfill, *Annual Report of Project Contributions to NE-60* (October 1986), report that LMF neutralized Rous sarcoma virus when administered in combination therewith to nine day old SPAFAS egg embryos as measured by chorioallantoic membrane pock formation. The present application is based upon our continuing investigation into the activity of LMF.

Gyles and Whitfill, *Annual Report of Project Contributions to NE-60* (October 1987) report that LMF also has antiviral activity against Infectious Bursal Disease Virus and Infectious Bronchitis Virus.

SUMMARY OF THE INVENTION

The present invention provides low molecular weight antiviral factors and methods of purifying the same. The present invention also provides compounds that can be used to treat and/or prevent infectious bursal disease and infectious bronchitis disease. The present compound also provides methods of treating these diseases. Moreover, the present invention provides compounds having antimicrobial activity.

The low molecular weight anti-viral factors of the present invention can provide a new vaccine for the treatment and/or prevention of diseases in poultry, other animals, and humans. Such diseases include, but are not limited to, those caused by retroviruses (i.e., RNA type), and malignant tumors (i.e., cancer). Of course, the human immunodeficiency virus (HIV) and its variants and relatives which cause AIDS (acquired immune deficiency syndrome) and AIDS-like diseases are the classic example. Diseases caused by molds and bacteria are also envisioned for possible prevention and/or treatment.

In an embodiment, the vaccine comprises a disease agent, such as the virus, plus at least one low molecular weight anti-viral factor in a suitable carrier.

The low molecular weight anti-viral factors are produced through a genetically selected Regressor Line of chickens. Blood serum is taken from these chickens and is biochemically separated into factors that include the low molecular weight anti-viral factors.

The low molecular weight anti-viral factors of the present invention can also be used alone to treat diseases caused by, but not limited to, retroviruses, also types of cancer, and diseases caused by molds and bacteria. In this regard, the low molecular weight anti-viral factors have been demonstrated to possess antiviral activity against Newcastle disease virus (NDV), infectious bursal disease virus (IBDV), and infectious bronchitis virus (IBV). Low molecular weight anti-viral factors have been found to also possess antibacterial activity against *Pasteurella multocida*, and antimold activity against *Aspergillus fumigatus*. Growth promotion of chicken fibroblasts has been demonstrated by the low molecular weight anti-viral factors and the vaccine potential of low molecular weight anti-viral factors and Rous sarcoma virus has been demonstrated.

Alternatively stated, an aspect of the present invention is a method of protecting a bird against infectious bursal disease virus (IBDV). The method comprises administering the bird IBDV in combination with low molecular weight viral neutralizing factor (LMF). IBDV is administered in an amount effective to induce an immune response, and LMF is administered in an amount effective to protect the bird from infection by the IBDV.

Another aspect of the present invention is a pharmaceutical composition useful for protecting a bird against IBDV. The composition comprises IBDV in combination with LMF in a pharmaceutically acceptable carrier. IBDV is provided in an amount effective to induce an immune response in a bird, and LMF is provided in an amount effective to protect such a bird against infection by the IBDV.

Still another aspect of the present invention is a method of protecting a bird against infectious bronchitis virus (IBV). The method comprises administering the bird IBV in combination with LMF. The IBV is administered in an amount effective to induce an immune response, and the LMF is administered in an amount effective to protect the bird from infection by the IBV.

Still another aspect of the present invention is a pharmaceutical composition useful for protecting a bird against IBV. The composition comprises IBV in combination with LMF in a pharmaceutically acceptable carrier. IBV is provided in an amount effective to induce an immune response in a bird, and LMF is provided in an amount effective to protect such a bird against infection by the IBV.

A final aspect of the present invention is a method of treating a microbial infection in an animal. The method comprises administering to the animal LMF in an amount effective to reduce the microbial infection in the animal.

Additional features and advantages of the present invention will be apparent from the detailed description of the presently preferred embodiments.

DETAILED DESCRIPTION OF THE PRESENTLY PREFERRED EMBODIMENTS

The present invention relates to low molecular weight anti-viral factors and methods of producing the same. The low molecular weight anti-viral factors can be used as a vaccine or treatment for disease states. Depending on requirements, only one low molecular weight factor or a plurality of factors can be used.

Although in some embodiments of the low molecular weight anti-viral factors of the present invention they are directed to the Rous sarcoma virus, there are other disease agents that may be used to produce other low molecular weight anti-viral factors as a response from the host that is challenged. Hence like vaccines, curative, or treatment compositions are possible. In this regard, the anti-viral low molecular weight factor(s) may be used as a model to challenge chickens with other pathogens and to search for and isolate and purify other low molecular weight factors that may be evoked by the host chicken in response to other specific pathogens. These additional low molecular weight factors would be purified, and their biological activity determined for usefulness in the prevention and cure of diseases of chickens, other animals, and humans.

The invention also broadly includes processes for producing low molecular weight anti-viral factors. In an embodiment, the method includes the use of chickens that have the genetic abilities to cause regression of Rous sarcoma virus. The Rous sarcoma virus is a retrovirus (RNA type) and the chickens were typically challenged with Rous sarcoma virus subcutaneously. In some cases, the chickens were rechallenged with Rous sarcoma tumor homogenate at repeated time intervals to give enhanced low molecular weight anti-viral factors. This is referred to as the regression line of chickens. As set forth in detail below, these chickens have been genetically selected for years and have the ability to cause spontaneous remission of malignant Rous sarcoma tumors.

The term "animals," as used herein, is intended to include, among other things, mammals, such as mice, rats, guinea pigs, rabbits, ferrets, dogs, cats, cows, horses and primates including man. Also encompassed within the term animals are both fish and birds. The term "bird" is intended to include males or females of any avian species, but is primarily intended to encompass poultry which are commercially raised for eggs or meat. Accordingly, the term "bird" is particularly intended to encompass hens, cocks and drakes of chickens, turkeys, ducks, quail and pheasant.

The term "low molecular weight viral neutralizing factor," as used herein, means the low molecular weight compound obtained from sera of birds which regress tumors induced by a Rous sarcoma virus (RSV) challenge after RSV challenge. Low molecular weight viral neutralizing factor (LMF) is characterized by an ability to block pock formation by Rous sarcoma virus on bird embryo chorioallantoic membranes, as explained in detail below. LMF may be produced in accordance with procedures known in the art, as explained in the Examples which follow.

LMF is prepared for mixture with virus and inoculation into birds in a pharmaceutically acceptable carrier. LMF and virus are prepared in sodium phosphate-buffered saline (pH 7.4) or conventional media such as MEM. The carrier media containing LMF also contains the virus for inducing the immune response in the animal.

The term "Infectious Bursal Disease Virus" (IBDV), as used herein, encompasses all strains of IBDV. Exemplary are the Bursal Disease Vaccine, Lukert strain, live virus, which is obtained from either Vineland Laboratories in Vineland, N.J. or Salsbury Laboratories in Charles City, Iowa, and the Bursal disease virulent challenge virus, which is obtained from the U.S.D.A. in Ames, Iowa (original isolate from S. A. Edgar).

The term "Infectious Bronchitis Virus" (IBV), as used herein, encompasses all strains of IBV. Exemplary are Mass. 41 Strain, Arkansas 99 Strain, Connecticut A5968, and Michigan State University Respository Code 42 Strain, all available from American Type Culture Collection, Rockville, Md.

The regressor line of chickens was developed as follows:

Giant Jungle Fowl were selected due to their high resistance to diseases. Research further confirmed an extraordinarily high degree of natural resistance in the Giant Jungle Fowl to challenges of Rous sarcoma virus, a member of the family of retroviruses, and to challenges of the virus on the chorioallantoic membrane of the chick embryos. It was further felt that there was a high probability that the Giant Jungle Fowl growing chickens had the capacity to cause the spontaneous remission of a single malignant Rous sarcoma, because as an embryo, it often allowed no small tumors or a very small number of tumors to grow on the chorioallantoic membrane. However, the Giant Jungle Fowl laid few eggs.

The Giant Jungle Fowl was crossed with the White Leghorn chicken, which laid a large number of eggs. The genes for regression of the Giant Jungle Fowl were therefore combined with those of egg production from the White Leghorn by $F_1$ and $F_2$ crosses, the $F_1$ crossed offspring were challenged with Rous sarcoma virus. Those that regressed tumors were used as parents of the next generation. This was followed in a similar manner in each subsequent generation thereby causing an intense selection for regression of Rous sarcomas over six generations, and then continued to 12 generations.

From this genetic selection for the ability to regress tumors, a new line of chicken capable of regressing tumors and also having high egg producing ability was developed and is called the Regressor Line. A model for investigating the regression phenomenon was established. The Regressor Line chickens either regressed tumors or were withstanding tumors at the end of a long period of observation, in 89.6% of the chickens. In contrast, the Progressor Line (White Leghorn) permitted progressive tumor growth in over 90% of the chickens. This model was further refined by blood typing each line. Four sublines, each pure for a different blood group, were developed and maintained. They are symbolized by $B^1B^1R$, $B^2B^2R$, $B^3B^3R$ and $B^4B^4R$ for the regressor sub-lines, and $B^1B^1Pr$, $B^2B^2Pr$, $B^3B^3Pr$ and $B^4B^4Pr$ for the progressor sub-lines. This was an improvement because each blood group has a different interaction with the genes for regression and progression of tumors.

A low molecular weight isolate (low molecular weight anti-viral factors) has been obtained from the blood serum of the Regressor line chickens that have been further immunized by subsequent challenges with Rous sarcoma tumor homogenate. These chickens are referred to as the Hyperimmune Regressor line. Anti-viral activity by this isolate was made from peak IV off a G-25 Sephadex column (a $31 \times 8$ cm G-25 column). Although the anti-viral activity was initially found against Rous sarcoma virus (Rous sarcoma virus) it has also been found against Newcastle disease virus (NDV-La Sota).

Biogel P-2 acrylamide chromatography was used to further purify the G-25 peak IV. To this end, the mixture of sera components contained in the G-25 peak IV were passed through a Biogel P-2 acrylamide column. The peak I from Biogel P-2 contained the anti-Rous sarcoma virus and anti-NDV activity. Anti-viral activity against infectious bursal disease virus (IBDV-Lukert strain) and infectious bronchitis virus (IBV-Mass.41 strain) has been found using the low molecular weight anti-viral factors as peak I from Biogel P-2. A small initial peak may lead to the peak containing LMF being identified as peak II. Since this peak is small, and is not always present, it is preferred to identify the active peak as peak I.

Microtiter tissue culture using ten day old SPAFAS chicken embryo fibroblasts was used for viral assays using IBDV. A $10^1$ dilution of the original stock IBDV in 50 ul volume was titered to kill 100% of the cells in microtiter wells. When 200 ug low molecular weight anti-viral factors in 40 ul of PBS was preincubated with IBDV, complete neutralization of IBDV resulted. No killing of the chicken fibroblasts with the low molecular weight anti-viral factors-IBDV conjugate was seen after staining as compared to viral controls.

A $10^{-2}$ dilution of stock IBV was titered to cause stunting of growth of nine day old SPAFAS embryos by 50% as compared to controls. However, when 200 ug low molecular weight anti-viral factors in 40 ul PBS was incubated with this dose of IBV, complete protection to the embryos was seen whereas the controls receiving IBV were stunted 50% by weight.

A $10^{-2}$ dilution of laryngotracheitis virus (LT) was used to cause significant thickening of the CAM's on nine day old SPAFAS embryonated eggs. A 200 ug amount of low molecular weight anti-viral factors in 100 ul of PBS was incubated with this dose of LT and the mixture inoculated on the nine day old CAM's. No significant anti-viral activity was seen with low molecular weight anti-viral factors against a $10^{-2}$ dilution of LT.

Using zone of inhibition assays on standard agar, it was found that against a 1 McFarland concentration of bacteria or mold, that 150 ug of low molecular weight anti-viral factors demonstrates preliminary antimicrobial activity. A 1.5 cm zone of inhibition was seen against *Pasteurella multocida,* 0.5 to 1.0 cm zone against *Aspergillus fumigatus*. Muller Hinton agar was used for bacteria and Sabaroud Dextrose agar was used for the mold.

Low molecular weight anti-viral factors maintain similar Rous sarcoma virus anti-viral activity at pH 6.0, 7.0, and 8.0, and at temperature ranges from 4° C. to 80° C. However, when low molecular weight anti-viral factors are heated for 30 minutes at 90° C., it begins to lose anti-viral activity. At 90° C., approximately 50% of the anti-viral activity of low molecular weight anti-viral factors is destroyed after 30 minutes of heating. It was determined, as against a standard dose of Rous sarcoma virus capable of producing an average of 500 pocks per CAM, that as little as 10 ug of low molecular weight anti-viral factors could cause complete neutralization of that dose of Rous sarcoma virus.

It has been demonstrated that the viral neutralizing activity of low molecular weight anti-viral factors includes Rous sarcoma virus, NDV, IBV, and IBDV. All of these viruses are enveloped RNA viruses. Because no activity was shown against LT, a DNA virus, it suggests that low molecular weight anti-viral factors has a specificity for RNA viruses.

By way of example, and not limitation, the following steps can be used to extract, isolate, and partial purify the low molecular weight factor(s).

1. Blood is taken from Hyperimmune regressor chickens (to Rous sarcoma virus) by cardiac puncture.
2. The serum is obtained by centrifugation.
3. The serum is passed through a fine grade 31×8 cm G-25 Sephadex column. The low molecular weight factor(s) with anti-Rous sarcoma activity is found in peak 4 off the column.
4. Further purification is done by passaging the peak 4 isolate through Biogel P-2 acrylamide chromatography. The peak I from the Biogel P-2 column is found to contain the low molecular weight factor(s) with anti-Rous sarcoma virus, anti-Newcastle disease virus, anti-infectious bursal disease virus, and anti-infectious bronchitis virus activity. In addition, it has activity against some molds and some bacteria. It also shows promise to be useful in preparing improved vaccines, and as a growth promoter in tissue cultures of chick fibroblasts.

Upon purification and chemical characterization, the low molecular weight factor(s) can be synthesized in bulk quantities for in vivo use on chickens, animals and humans, against all retroviruses and other pathogens, and to make vaccines for prevention of diseases. Furthermore, the structure and sequence of the amino-acids may be changed and re-arranged to produce new modified low molecular weight factors with enhanced use against retroviruses and other pathogens, and for improved vaccines to prevent diseases in chickens, animals, humans and perhaps plants on earth and in space, and to use in treatments to cure diseases of chickens, animals, humans and perhaps plants on earth and in space.

With the purified low molecular weight factor(s), monoclonal antibodies to the low molecular weight factors can be produced that will reveal the tissues and cells in which it is produced so that its exact metabolic pathway of action can be determined. This can open up new areas of research and new products for prevention and cure of diseases as well as the identification of pathogens.

The low molecular weight factor(s) may be extracted from the regression fluid that collects at the site of regression of a Rous sarcoma. These additional low molecular weight factors would be purified and the biological activity of these low molecular weight anti-viral factors and/or their synthetic derivatives determined for usefulness in the prevention and cure of diseases of chickens, other animals, and humans, and for the diagnostic identifications of pathogens.

The low molecular weight anti-viral factors may be extracted from tissues and/or cells such as, for example, but not restricted to, sensitized lymphocytes and macrophages from the bloodstream or at the site of a regressing Rous sarcoma or from the peritoneum. These additional low molecular weight factors would be purified and the biological activity of these low molecular weight anti-viral factors or their synthetic derivatives determined for usefulness in the prevention and treatment of diseases of chickens, other animals, and humans, and for the diagnostic identification of pathogens.

Birds are administered LMF and virus by any suitable means. Exemplary are by oral administration, by intramuscular injection, by subcutaneous injection, by intravenous injection, by intraperitoneal injection, by eye drop or by nasal spray. The birds may be hatched birds, including newly hatched, adolescent, or adult birds. The birds may be in ovo, as described in U.S. Pat. No. 4,458,630 to Sharma, the disclosure of which is to be incorporated herein by reference.

Virus is administered as a mixture to birds in an amount sufficient to evoke an immune response to the virus. The term "immune response," as used herein, means any level of protection from subsequent exposure to the virus which is of some benefit in a population of birds, whether in the form of decreased mortality, decreased lesion scores, improved feed conversion ratios, or the reduction of any other detrimental effect of the disease, regardless of whether the protection is partial or complete.

The quantity of the virus is such that, when mixed with LMF and administered together, an immune response to the virus will result. The quantity of LMF administered in combination with the virus need not, however, be sufficient to provide complete protection from the virus, as long as the detrimental response produced by the virus is reduced to a level at which the benefits of the immune response produced outweigh any harm resulting from the infection.

Microbial infections treated by the present invention include infections of bacterial, mycoplasma, fungal, and protozoan origin. Exemplary infectious bacteria include *Escherichia coli, Salmonella typhimurium* and *Pasteurella multocida*. Exemplary of disease-causing fungi is *Aspergillus fumigatus*. Exemplary mycoplasma are *Mycoplasma synoviae* and *Mycoplasma gallisepticum*. The term "protozoan" is intended to include those members of the subphyla Sarcomastigophora and Sporozoa of the phylum Protozoa. More particularly, the term "protozoan" as used herein is intended to include those genera of parasitic protozoa which cause disease in man or domestic animals. These genera are, for the most part, found classified in the superclass of Mastigophora of the subphylum Sarcomastigophora and the class of Telosporea of the subphylum Sporozoa in the classification according to Baker (1969). Illustrative genera of these parasitic protozoa include Histomonas, Trypanosoma, Giardia, Trichomonas, Eimeria, Isopora, Toxoplasma and Plasmodium. Of particular interest are protozoans of the genus Eimeria, which cause avian coccidiosis.

For the treatment of microbial infections LMF may be administered in a pharmaceutically acceptable carrier by any suitable route, as described in connection with the use of LMF for protection against viral infections above.

The present invention is described in greater detail in the following Examples. These examples are provided for illustrative purposes only, and are not to be taken as limiting.

EXAMPLE 1

Experimental Animals

The birds used for challenge with Rous sarcoma virus and subsequent sera collection were of the regressor chicken line described in Gyles et al., 46 *Poultry Sci.* 465 (1967).

EXAMPLE 2

Standard Inoculum of Rous Sarcoma Virus

A standard inoculum of RSV-RAV-1 to be used to stimulate the production of antiviral factor in regressor line chicken sera was prepared with an RSV-RAV-1 Bryan High Titer Strain identified as Lot #1 prepared for American Type Culture Collection in Rockville, Md. by Dr. John P. Bader, NCI, NIH. The titer was $2 \times 10^6$ PFU per milliliter and was stored at $-70$ degrees Celsius before use. Inoculation of birds was accomplished by infecting a standard inoculum of 0.1 milliliter of diluted RSV-RAV-1 into the left wing web as described in Whitfill et al., 61 *Poultry Sci.* 1573 (1981).

EXAMPLE 3

Preparation of R-Line Hyperimmune Sera

The object of this example was to prepare tumor homogenate from susceptible chickens to be used to boost regressor chickens to induce production of antiviral factor from hyperimmune sera. R-line chickens were challenged with a standard inoculum of RSV, and after complete tumor regression as measured by visible disappearance of tumors, birds were injected once weekly for at least three weeks with a standard inoculum of Rous sarcoma tumor homogenate (RSTH) booster. Five days after the last booster RSTH injection, 20 milliliters of blood was removed from each chicken by cardiac puncture and allowed to clot for one hour at room temperature. Clotted blood was sedimented at $3000 \times g$ at room temperature in a Sorvall centrifuge for ten minutes and hyperimmune sera was removed and stored at 5 degrees Celsius. This routine was continued for several weeks on a given group of donor regressor chickens.

EXAMPLE 4

Preliminary Purification of Low Molecular Weight Antiviral Factor (LMF)

The object of this example was to partially purify the antiviral factor from a large volume of hyperimmune regressor line chicken sera. Approximately 400 milliliters of R-line hyperimmune sera prepared according to Example 3 above was applied to a Sephadex G-25 fine column (8×35 centimeters) and eluted at 250 milliliters per hour with 0.005M sodium phosphate buffer, pH 7.0. Four peaks were eluted from the column and peak IV, the last to elute at 2800 milliliters, contained the LMF activity against RSV-RAV-1. Peak IV was shown to neutralize RSV-RAV-1 by incubation with the virus with subsequent injection into wing-webs of susceptible chickens, as previously described for Sephadex G-100 fraction II. See Whitfill et al., 61 *Poultry Sci.* 1573 (1981). Peak IV typically eluted in a total volume of 1000 milliliters of buffer at 28 milliliters per tube and was freeze dried and redissolved at a concentration of 100 milligrams per milliliter in sterile distilled water.

EXAMPLE 5

Further Purification of Sephadex G-25 Peak IV Utilizing Biogel P-2 Column Chromatography The object of this Example was to further purify and desalt antiviral factors from earlier preliminary active fractions utilizing gel filtration column chromatography and to prepare stock solutions of the active antiviral fraction to be used in further tests.

Approximately 35 milliliters of redissolved Sephadex G-25 peak IV (3500 milligrams) obtained as described in Example 4 above was applied to a biogel P-2 column (5 centimeters×40 centimeters), and eluted in distilled water at a flow rate of 90 milliliters per hour. The antiviral activity was found against RSV-RAV-1 in the first peak (Peak I) eluting at the void volume after 390 milliliters at 14 milliliters per tube. This peak I, eluting in a total volume of 100 milliliters, was freeze dried to dryness and the salt free preparation represented the more highly purified preparation of LMF. Approximately 5–10 milligrams of further purified LMF typically resulted from peak I of the biogel P-2 column. A stock solution of the LMF in phosphate-buffered saline or distilled water was freshly prepared to a concentration of 5 milligrams per milliliter before testing for activity.

One activity unit for this stock solution is defined as the amount of activity against Rous sarcoma virus in one milliliter of this LMF solution. One milliliter of this solution will completely neutralize 500 standard doses of Rous sarcoma virus. A standard dose of Rous sarcoma virus is defined as that dilution of virus in 100 microliters that will produce an average of 70 pocks on SPF nine day old embryo chorioallantoic membranes by day 16. LMF is not toxic to a preparation $7 \times 10^4$ chicken fibroblasts until a dose level of 0.1 Activity Units is reached.

EXAMPLE 6

Viral Neutralizing Activity of LMF Against Infectious Bursal Disease Virus

The object of this Example was to determine if the antiviral factor can neutralize infectious bursal disease virus (Lukerts Strain) in microtiter tissue culture using SPF chicken fibroblasts.

LMF material isolated by biogel P-2 chromatography as described in Example 5 above was used in this experiment. A stock solution of 5 micrograms per microliter of LMF prepared in phosphate-buffered saline (PBS) was prepared to test for activity against IBDV.

Microtiter tissue culture using ten day old SPAFAS chicken embryo fibroblasts was used for viral assays using IBDV by standard techniques. See Skeeles, 23 *Avian Diseases* 95 (1979). A $10^1$ dilution with PBS of the original stock IBDV in 50 microliter volume was determined by titering to kill 100% of the cells in microtiter wells. When 200 micrograms LMF in 40 microliters of PBS was preincubated with 50 microliters of $10^1$ dilution of IBDV, complete neutralization of IBDV resulted. No killing of the chicken fibroblasts with the LMF-IBDV conjugate was seen after staining as compared to viral controls.

The Lukert Strain of IBDV was obtained from Dr. Kirk Skeeles, University of Arkansas, Fayetteville, Ark. for the microtiter assays. Chicken fibroblasts were prepared in MEM media from SPF ten day old chicken embryos.

In a typical experiment, 200 microliters of fibroblasts (approximately $7.0 \times 10^4$ cells) were added to rows 1–4, 8 wells each, on a microtiter plate. Each well in row 1 received 90 microliters PBS and served as a control well. Each well in row 2 received 40 microliters LMF stock solution (200 micrograms) and served as the LMF treated well. Each well in row 3 received 50 microliters of a $10^1$ dilution of the stock IBDV and served as the virus treated well. Each well in row 4 received 90 milliliters of a mixture composed of 50 microliters of $10^1$ IBDV plus 40 microliters LMF and served as the LMF-IBDV conjugate treated well. The LMF and IBDV mixture were allowed to incubate for twenty minutes on ice before addition to fibroblasts. IBDV and LMF were also each kept on ice before addition to fibroblasts. The plates were incubated at 37 degrees Celsius for three days and then fixed with ethanol and stained with crystal violet for examination.

It was concluded from the results of these experiments that 200 micrograms LMF completely neutralized a $10^1$ dilution of Lukerts Strain IBDV because the cells in row 4 that received the LMF-IBDV conjugate were not infected and therefore identical to those that received PBS in the control group. The healthy living cells were adhered to the bottom of the microtiter well and readily stained. The wells in row 3 that received the IBDV were absent of cells due to cell death and release from the plates, and hence showed no staining. The cells in row 2 that received LMF demonstrated increased staining and hence increased growth rate as compared to the controls that received PBS only. LMF at 200 micrograms per well was not toxic to the fibroblasts.

EXAMPLE 7

Viral Neutralizing Activity of LMF Against Infectious Bronchitis Virus (IBV)

The object of this Example was to determine if LMF can neutralize infectious bronchitis virus (Mass. 41 Strain) utilizing nine day old SPF embryonated eggs.

The LMF material isolated by biogel P-2 chromatography described in Example 5 was used in this experiment and the standard stock solution of IBV was used.

A $10^2$ dilution of stock IBV was determined by titering to cause stunting of growth of nine day old SPAFAS embryos by approximately 40–50% by day 16 as compared to controls. However, when 200 micrograms of LMF in 40 microliters PBS was incubated with this dose of IBV, complete protection to the embryos (no stunting) was seen whereas the controls receiving IBV were stunted 50% by weight. Hence, LMF neutralized the IBV dose and prevented stunting.

The Mass. 41 Strain of IBV was obtained from Dr. Kirk Skeeles, University of Arkansas, Fayetteville, Ark. for the embryo stunting assay. Inoculation of embryonated eggs for stunting was performed by standard procedure. See Lukert, in *Isolation and Identification of Avian Pathogens,* 70 (2d ed. 1980) (Creative Printing Co., Endwell, N.Y.). This involved injection of IBV solution into the allantoic sac of nine day old embryonated eggs. Expected by day 16 is stunting of the embryo if the titer of virus used is correct. The eggs are placed in an egg incubator at 37 degrees Celsius after injection and then removed, chilled, and embryos inspected on day 16.

In a typical experiment, the SPF nine day old embryonated eggs in group 1 were each injected with 100 microliters PBS and served as the control group. The eggs in group 2 each received 100 microliters of a $10^2$ dilution of IBV and served as the virus treated group. The eggs in group 3 each received 140 microliters of a mixture composed of 100 microliters of $10^2$ diluted IBV plus 40 microliters LMF (200 micrograms) and served as the LMF virus conjugate group. The LMF plus IBV mixture were allowed to incubate for twenty minutes on ice before inoculation to the embryonated eggs. The embryos were killed by chilling and removed from the egg and weighted on day 16. The weights of the three groups were compared. The PBS control group and LMF plus IBV treated group were of near equal weight whereas the IBV treated group were reduced 43% by weight.

These experiments demonstrated that 200 micrograms LMF completely neutralized a $10^2$ dilution of Mass. 41 IBV Strain by completely preventing stunting of the embryos in group 3.

EXAMPLE 8

Viral Neutralization of a USDA Standard Challenge IBDV Strain in the Chickens with Subsequent Immunization Potential The object of this Example was to determine if LMF can viral neutralize a USDA standard challenge strain of infectious bursal disease virus and if the inoculation of the virus-LMF factor conjugate can stimulate immunity to a follow up dose of challenge IBDV strain.

The LMF material isolated in Example 5 was used in this Example. These data indicate the immunizing potential of the LMF-IBDV complex and confirm the viral neutralizing activity of LMF against a USDA Standard Challenge IBDV Strain in the live chicken.

Lot #81-1 of USDA Standard Challenge IBDV Strain was obtained from Dr. Kirk Skeeles, University of Arkansas, Fayetteville, Ark. The stock virus, which is $10^{3.8}$ EID50 per milliliter, was diluted 1:10 or $10^1$ dilution in the experiment. On day 0, the four week old SPF white leghorn chickens in group 1 (six chickens) received 40 microliters by eye drop in each eye of the $10^1$ diluted IBDV and were the virus treated group. Also on day 0, the chickens in group 2 (six chickens) received a mixture by eye drop in each eye composed of 40 microliters $10^1$ diluted IBDV plus 40 microliters LMF (200 micrograms) and were the LMFIBDV conjugate treated group. Group 3 (six chickens) served as the uninoculated control. On day 9 after initial treatment, half the chickens in group 1 were necropsied and half the birds in groups 2 and 3 were necropsied and bursas examined. In the virus treated group 1, all bursas were atrophied (visual examination), whereas in the LMF-IBDV conjugate treated group 2 the bursas were slightly enlarged (visual examination), which suggested an immune response. Group 3 had normal bursas in size and appearance. The remaining half of the chickens in groups 1 and 2 subgrouped as groups 1A and 2A, were rechallenged on day 17 with 40 microliters of a $10^1$ dilution of IBDV challenge strain in each eye to determine if the initial LMF-IBDV eye drop mixture on day 0 could induce greater immunity, as compared to the group receiving IBDV alone. On day 35, the chickens in subgroups 1A and 2A and 3 were examined. Ratios of bursa and spleen weight to total body weight of control chickens in group 3 were established. The IBDV and IBDV plus LMF treated birds were compared on day 35 according to their spleen and bursa weight to body weight ratios.

It was determined from the control birds that for bursa to body weight ratios that 0.92 or below represented atrophied bursa and 1.136 or greater represented hypertrophied bursa. For control spleen to body weight ratios that 0.79 or below represented atrophied spleen and 1.27 or greater represented hypertrophied spleen. Based on this, the IBDV group 1 showed two atrophied and one hypertrophied bursa and one normal, one atrophied, and one hypertrophied spleen. The IBDV and LMF group 2 showed one atrophied and two hypertrophied bursas and three normal spleens.

In conclusion, the IBDV and LMF inoculation protected the group 2 against a second challenge of IBDV better than birds that had not received the IBDV-LMF inoculation before IBDV challenge as in group 1. Hence, indicating that LMF when combined with IBDV can induce a vaccine or immunizing potential in the live chickens against a second challenge of live virus.

EXAMPLE 9

Antimicrobial Activity of LMF

The object of this Example was to determine if LMF exhibits antimicrobial activity against bacteria and fungi.

Zone of inhibition assays were used to determine the activity of LMF prepared as in Example 5 against *Pasteurella multocida* and *Aspergillus fumigatus* by standard techniques. See McAllister, in *Diagnostic Procedures in Veterinary Bacteriology and Mycology,* 347 (G. R. Carter 3d ed. 1979). The zone of inhibition is defined as the zone free of organisms after placing a disc containing 150 micrograms of LMF on the agar surface which has been streaked with 1 McFarland of the organism.

For *P. multocida,* 1 McFarland of the organism was used to produce a bacterial lawn on Muller Hinton agar. A 1 centimeter diameter filter paper disc was saturated and dried with 30 microliters LMF (150 micrograms) and placed in the bacterial lawn. The plate was incubated at 37 degrees Celsius for 48 hours and examined. A 1.5 centimeter zone of inhibition was seen against *P. multocida* indicating antibacterial activity.

For *A. fumigatus,* 1 McFarland of the organism was used to produce a fungal lawn on Sabaroud Dextrose agar. A 1 centimeter filter paper disc was saturated with 30 microliters (150 micrograms) LMF, dried, and placed in the fungal lawn. The plate was incubated at room temperature for 72 hours and examined. A 0.5 centimeter zone of inhibition was seen against *A. fumigatus*, indicating antifungal activity.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A composition useful in preventing infectious bursal disease in an animal, the composition produced by isolating from the blood serum of a hyperimmune regressor line chicken at least one low molecular weight factor, obtained by taking peak IV off a G-25 Sephadex column, further purifying the mixture contained in the peak IV column by passage through a Biogel P-2 acrylamide column and taking peak I and combining peak I with an effective amount of a virus that causes infectious bursal disease.

2. A composition useful in preventing infectious bronchitis disease, the composition produced by isolating from the blood serum of a hyperimmune regressor line chicken at least one low molecular weight factor, obtained by taking peak IV off a G-25 Sephadex column, further purifying the mixture contained in the peak IV column by passage through a Biogel P-2 acrylamide column and taking peak I, and combining peak I with an effective amount of a virus that causes infectious bursal disease.

3. A method of preventing infectious bursal disease in an animal comprising the steps of:
taking blood serum from a hyperimmune regressor line chicken;
isolating from the blood serum a low molecular weight factor by purifying the serum by taking peak IV off a G-25 Sephadex column;
further purifying the mixture contained in the peak IV column by passage through a Biogel P-2 acrylamide column and taking peak I; and
combining a virus for infectious bursal disease with the product of peak I and administering to the animal the resultant product.

4. A method of preventing infectious bronchitis disease in an animal comprising:
taking blood serum from a hyperimmune regressor line chicken;
isolating from the blood serum a low molecular weight factor by purifying the serum by taking peak IV off a G-25 Sephadex column;
further purifying the mixture contained in the peak IV column by passage through a Biogel P-2 acrylamide column and taking peak I; and
combining a virus for infectious bronchitis disease with the product of peak I and administering to the animal the resultant product.

5. The method of claim 3 wherein said animal is a bird and said composition is administered in an amount effective to induce an immune response.

6. A method according to claim 5, wherein said bird is a hatched bird.

7. A method according to claim 6, wherein said bird is in ovo.

8. A composition according to claim 1, wherein said low molecular weight factor is included in an amount of from about 100 to about 0.002 Activity Units per unit dose.

9. The method of claim 4 wherein said animal is a bird and said composition is administered in an amount effective to induce an immune response.

10. A method according to claim 9, wherein said bird is a hatched bird.

11. A method according to claim 9, wherein said bird is in ovo.

12. A composition according to claim 2, wherein said low molecular weight factor is included in an amount of from about 100 to about 0.002 Activity Units per unit dose.

* * * * *